US006939294B2

(12) United States Patent
Abe

(10) Patent No.: US 6,939,294 B2
(45) Date of Patent: Sep. 6, 2005

(54) ENDOSCOPE APPARATUS ALLOCATING FUNCTIONS OF SWITCHES BY ENDOSCOPE

(75) Inventor: Kazunori Abe, Saitama (JP)

(73) Assignee: Fujinon Corporation, Saitama (JP)

( * ) Notice: Subject to any disclaimer, the term of this patent is extended or adjusted under 35 U.S.C. 154(b) by 188 days.

(21) Appl. No.: 10/384,725

(22) Filed: Mar. 11, 2003

(65) Prior Publication Data

US 2003/0187327 A1 Oct. 2, 2003

(30) Foreign Application Priority Data

Mar. 26, 2002 (JP) ........................................ 2002-086716

(51) Int. Cl.[7] ............................ A61B 17/00; A61B 1/00
(52) U.S. Cl. ........................................ 600/131; 600/118
(58) Field of Search ................................ 600/101, 118, 600/158–159, 167–168; 341/22–23, 25

(56) References Cited

U.S. PATENT DOCUMENTS

| | | | | |
|---|---|---|---|---|
| 5,159,446 A | * | 10/1992 | Hibino et al. | 358/98 |
| 5,481,264 A | * | 1/1996 | Kim | 341/20 |
| 5,870,035 A | * | 2/1999 | Bjernulf | 341/35 |
| 6,425,858 B1 | * | 7/2002 | Minami | 600/168 |
| 6,758,807 B2 | * | 7/2004 | Minami | 600/168 |
| 2001/0026263 A1 | * | 10/2001 | Kanamori et al. | 345/156 |
| 2001/0039370 A1 | * | 11/2001 | Takahashi et al. | 600/159 |
| 2002/0025830 A1 | * | 2/2002 | Nishiyama et al. | 455/550 |
| 2003/0050533 A1 | * | 3/2003 | Minami | 600/168 |
| 2003/0194975 A1 | * | 10/2003 | Nishiyama et al. | 455/90.3 |

FOREIGN PATENT DOCUMENTS

| JP | 05-050725 | 3/1993 |
|---|---|---|
| JP | 09-276214 | 10/1997 |
| JP | 2000-271065 | 10/2000 |

* cited by examiner

Primary Examiner—John Leubecker
Assistant Examiner—Philip R Smith
(74) Attorney, Agent, or Firm—Snider & Associates; Ronald R. Snider

(57) ABSTRACT

An endoscope apparatus has an endoscope that is arranged to be connectable to a processor unit, and has a first, second and third operation switches provided on an operation section of the endoscope for operating various functions. The endoscope is provided with a rotary switch that is used to select one of combinations of predetermined functions allocated to the first, second and third operation switches. This allows any switch functions to be altered and defined only by the endoscope without cumbersome operations.

4 Claims, 3 Drawing Sheets

FIG. 4

| NO. | 1ST SW | 2ND SW | 3RD SW | NO. | 1ST SW | 2ND SW | 3RD SW |
|---|---|---|---|---|---|---|---|
| 1 | A | B | C | 9 | C | A | B |
| 2 | A | C | B | 10 | C | B | A |
| 3 | A | B | D | 11 | C | D | A |
| 4 | A | C | D | 12 | C | A | D |
| 5 | B | A | C | 13 | D | A | B |
| 6 | B | A | D | 14 | D | B | A |
| 7 | B | C | A | 15 | D | C | B |
| 8 | B | C | D | 16 | D | B | C |

ENDOSCOPE APPARATUS ALLOCATING FUNCTIONS OF SWITCHES BY ENDOSCOPE

BACKGROUND OF THE INVENTION

This application claims the priority of Japanese Patent Application No. 2002-86716 filed on Mar. 26, 2002 which is incorporated herein by reference.

1. Field of the Invention

The present invention relates to an endoscope, and more particularly to such an endoscope that allows for defining any functions of a plurality of operation switches disposed on an operation section of the endoscope.

2. Description of the Related Art

An endoscope apparatus provided with an electronic endoscope, a fiberscope and the like displays a motion image of an object taken through the endoscope, and is designed to perform various operations through the use of a plurality of operation switches such as a freeze, record (trigger), and magnification switch that are provided on an operation section of the endoscope. The freeze switch can display a still image of the object, the record switch can record moving images and the like of the object in a recording device such as a VTR, and the magnification (zoom) switch can display an optically or electronically magnified image of the object. These different switches are located on suitable positions of the operation section in view of frequencies of use etc.

Prior art endoscope apparatuses, however, suffer from a problem that locations of these switches are fixed and can not be changed, and therefore do not always contribute to ease of use. As such, it maybe desirable that these switches should be relocated when frequency of use of a switch varies depending on purposes of the endoscope, applied sites, and observed regions. There is also a need for conveniently defining locations of the operation switches according to tastes and preferences of the user, or practitioner. It would therefore be useful that functions of operation switches of an endoscope can be changed or customized by preference. This would provide an easy-to-use device.

Corresponding to the needs described above, it has been proposed to allow any functions of the switches provided on an operation section of an endoscope to be altered and defined by a processor unit, as described in Japanese Patent Publication No. 5-50725, Japanese Patent Laid-Open No. 9-276214, and Japanese Patent Laid-Open No. 12-271065.

These conventional apparatuses, however, require the user to operate a processor unit to alter and define the functions of the switches, resulting in cumbersome operations of altering and defining. An endoscope apparatus typically has more than one type of endoscopes connected to a processor unit as required. In this case, there is a problem that functions of switches must be redefined for each endoscope connected thereto.

The present invention has been made in view of the foregoing problems, and it is an object of the invention to provide an endoscope apparatus that allows the user to alter and define any functions of operation switches only by the endoscope without cumbersome operations using a processor unit.

SUMMARY OF THE INVENTION

To achieve the above object, the present invention according to Claim 1 is characterized in that it comprises: an endoscope having a plurality of operation switches for operating various functions, the plurality of operation switches being provided on an operation section thereof; a processor unit connected to the endoscope to process image signals; a selector switch for selecting one of a plurality of combinations of predetermined switch functions allocated to the plurality of operation switches, the selector switch being provided on the endoscope; and a control circuit for allocating switch functions of one of the combination selected by the selector switch to each of the operation switches, the control circuit being provided in the endoscope.

The invention according to Claim 2 is characterized in that the number of switch functions allocated by the selector switch is more than the number of the operation switches.

According to the arrangement described above, an operation section of an endoscope is provided with, for example, a rotary switch as a selector switch, and the rotary switch is used to select a combination of switch functions. For example, assuming that first, second and third switches are provided on an operation section of the endoscope, and any of freeze, record (trigger), magnification and iris functions may be set to the three operation switches as their switch functions, there may be 16 combinations of switch functions allocated to these three operation switches as shown in the following FIG. 4, and one of these 16 combinations may be selected using the selector switch. This enables a user to alter the function of each operation switch by preference and set, for example, the freeze function to the first operation switch, the magnification function to the second operation switch, and the iris mode function to the third operation switch.

BRIEF DESCRIPTION OF THE DRAWINGS

FIG. 4 shows some combinations of functions allocated to first, second and third operation switches in the embodiment.

DETAILED DESCRIPTION OF THE PREFERRED EMBODIMENTS

Figure 1:
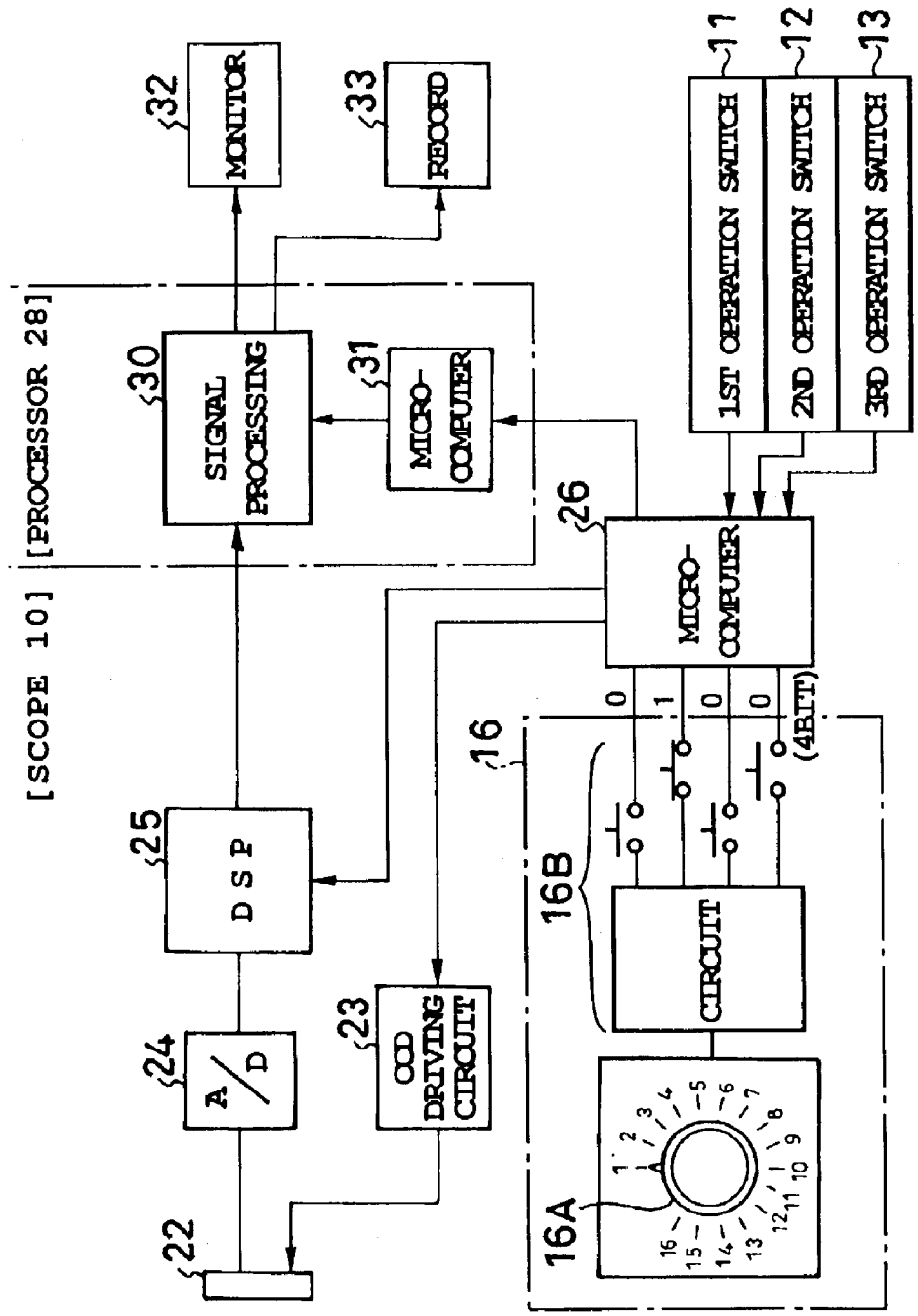
FIG. 1 shows a circuit block diagram illustrating an entire arrangement of an endoscope according to an embodiment of the present invention.
Figure 2:
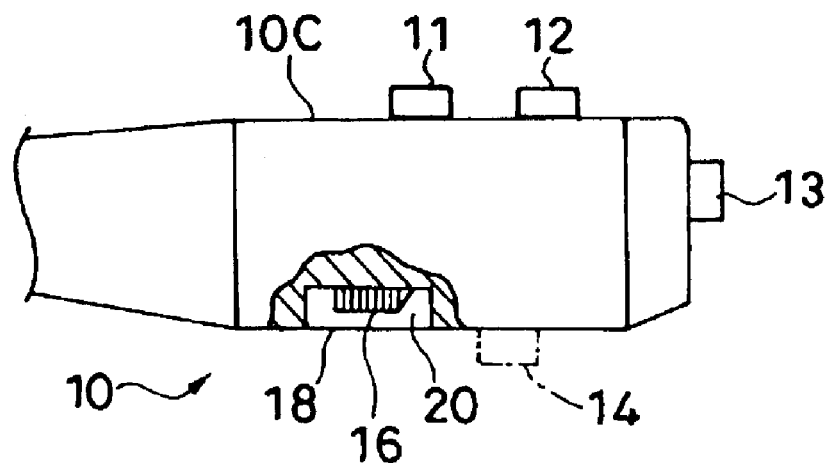
FIG. 2 shows an arrangement of the embodiment of an operation section of the endoscope.
Figure 3:
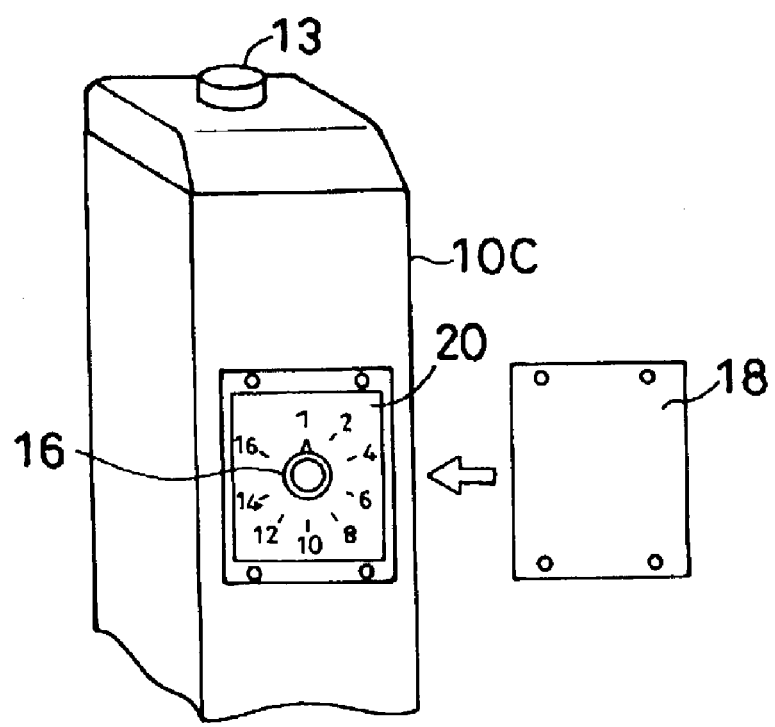
FIG. 3 shows the operation section of FIG. 2 vertically standing to reveal the bottom surface.

FIG. 1 shows an entire arrangement of an endoscope according to an embodiment of the invention, and FIGS. 2 and 3 show an arrangement of an operation section of the endoscope. In FIG. 2, an operation section 10C of an endoscope (scope) 10 is provided with, for example, a first operation switch 11, a second operation switch 12, and a third operation switch 13. In this embodiment, a freeze function A for displaying still images, a record function B for recording (trigger output) to a device that records in a form of a hard copy etc., an image magnification (zoom) function C for optically and/or electronically magnifying images, and an iris mode function D for specifying predetermined exposure conditions to control an amount of light are allocated to the first, second and third operation switches 11 to 13. A rotary switch 16 is provided on the bottom surface of the operation section 10C of FIG. 1 as a selection switch for altering and defining the switch functions.

FIG. 3 shows the operation section 10C of FIG. 1, revealing the bottom surface. The operation section 10C is provided with a compartment 20 having a cover 18. The cover 18 and compartment 20 are hermetically sealed to each other, providing an airtight compartment 20, in which in turn the rotary switch 16 is located. The rotary switch 16 is chosen such that 16 combinations of switch functions are selected using, for example, a 4-bit output.

In FIG. 1, an endoscope 10 is provided with a solid-state imaging device or charge coupled device (CCD) 22 at the tip thereof, and a CCD driving circuit 23 is located therein for reading and driving signals from the CCD 22. It is also provided with an analogue to digital converter 24 for converting outputs from the CCD 22 into digital signals, a digital signal processor (DSP) 25 for producing color image signals based on the outputs from the analogue to digital converter 24, and the like. Although not shown in the drawing, if an optical zoom capability is provided, movable lenses may be incorporated in an objective optics on the tip of the endoscope 10 for optically magnifying images, and driving members would then be provided to move the movable lenses forward and backward.

The endoscope 10 is also provided with a microcomputer 26 for controlling the first, second and third operation switches 11 to 13 and rotary switch 16 as well as allocation of switch functions, and centrally controlling circuits within the endoscope 10. The rotary switch 16 is comprised of, for example, a thumb wheel 16A that selects numbers 1 to 16 and a switch circuit 16B, and outputs selected one of the numbers 1 to 16 through a 4-bit output to the microcomputer 26. The microcomputer 26 in turn sets functions to the first operation switch 11, second operation switch 12 and third operation switch 13 based on the selected number and outputs operated signals corresponding to the switch functions to each circuit.

FIG. 4 shows a relationship between numbers selected by the rotary switch 16 and functions allocated to the first, second and third operation switches 11 to 13. In this table, reference character A denotes a freeze function, B denotes a record (trigger output) function, C denotes an image magnification function, and D denotes an iris mode function.

A processor unit 28 shown in FIG. 1 is arranged to removably connect the endoscope 10 thereto. The processor unit 28 is provided with a signal processing circuit 30 that receives output signals from the DSP 25 and handles various processes such as producing of still images, electronic magnification, controlling of exposure conditions to control an amount of light, and the like, and is also provided with a microcomputer 31, etc. A part of processing of the signal processing circuit 30 may be performed by the DSP 25 in the endoscope 10. Image signals output from the signal processing circuit 30 are provided to a monitor 32, or a recording device 33 such as a VTR, hard copy device, data filing device and the like.

The embodiment comprises the arrangement described above, and functions of the first, second and third operation switches 11 to 13 are defined by the microcomputer 26 in FIG. 1 controlling based on selection of the rotary switch 16. When the rotary switch 16 selects the number 1 as shown in FIG. 3, therefore, the first operation switch 11 is set to the freeze function A, the second operation switch 12 to the record function B, and the third operation switch 13 to the image magnification function C, as shown in the row 1 in FIG. 4. Similarly, when the rotary switch 16 selects the number 12, the first operation switch 11 is altered and set to the image magnification function C, the second operation switch 12 to the freeze function A, and the third operation switch 13 to the iris mode function D, as shown in the row 12 in FIG. 4.

Operated signals of the first, second and third operation switches 11 to 13 are transferred from the microcomputer 26 to the microcomputer 31 as operated signals of defined functions. The system including the microcomputer 31 is then controlled to perform freeze, record, image magnification and iris mode functions.

According to the embodiment as described above, the rotary switch 16 provided on the operation section 10C of the endoscope can define any function of the first, second and third operation switches 11 to 13, completing altering and defining the switch functions within the endoscope 10. When a different type of an endoscope 10 is connected to the processor unit 28, therefore, switch functions can easily be changed without cumbersome operations using a processor unit in the conventional manner.

Although defining four functions to three switches, or the first, second and third operation switches 11 to 13, has been described in the embodiment described above, four or more operation switches may be provided, for example as an operation switch 14 in FIG. 2, and a switch function may be selected among five or more types of functions. As a selector switch, the rotary switch 16 is provided on the operation section 10C. The switch may be located in other area, for example, near a connector.

As described above, the embodiment effectively allows the user to alter and define any functions of operation switches only by the endoscope without cumbersome operations using a processor unit in the conventional manner.

What is claimed is:

1. An endoscope apparatus comprising:

an endoscope having a plurality of operation switches for operating various functions, said plurality of operation switches being provided on an operation section thereof;

a processor unit connected to said endoscope to process image signals;

a selector switch for selecting one of a plurality of combinations of predetermined switch functions allocated to said plurality of operation switches, said selector switch being provided on said endoscope;

a control circuit for allocating switch functions of one of the combination selected by said selector switch to each of said operation switches, said control circuit being provided in said endoscope; and wherein said predetermined switch functions are the same plurality of functions which are used in two or more combinations.

2. The endoscope apparatus according to claim 1, wherein the number of switch functions which the selector switch is capable of allocating is more than the number of said operation switches.

3. The endoscope apparatus according to claim 1, wherein a rotary switch is provided on the operation section of the endoscope as said selector switch.

4. The endoscope apparatus according to claim 1, wherein the predetermined switch functions are a freeze function, record function, image enlargement function and iris mode function, and allocate optionally to three or four operation switches.

* * * * *